US007486992B2

(12) United States Patent
Pufulescu et al.

(10) Patent No.: US 7,486,992 B2
(45) Date of Patent: Feb. 3, 2009

(54) BATTERY COVER ASSEMBLY

(75) Inventors: Mirela Pufulescu, Narraweena (AU); Edmond Capcelea, Bondi Junction (AU)

(73) Assignee: Cochlear Limited, Lane Cove (AU)

( * ) Notice: Subject to any disclaimer, the term of this patent is extended or adjusted under 35 U.S.C. 154(b) by 489 days.

(21) Appl. No.: 10/967,223

(22) Filed: Oct. 19, 2004

(65) Prior Publication Data

US 2005/0085871 A1 Apr. 21, 2005

(30) Foreign Application Priority Data

Oct. 20, 2003 (AU) ............................. 2003095730

(51) Int. Cl.
*A61N 1/18* (2006.01)

(52) U.S. Cl. ........................................................ 607/57

(58) Field of Classification Search ..................... 607/5, 607/10, 36, 57; 381/322-324, 328-330
See application file for complete search history.

(56) References Cited

U.S. PATENT DOCUMENTS 6,041,128 A * 3/2000 Narisawa et al. ............ 381/322

* cited by examiner

*Primary Examiner*—Angela D Sykes
*Assistant Examiner*—Rex Holmes
(74) *Attorney, Agent, or Firm*—Connolly Bove Lodge & Hutz LLP

(57) ABSTRACT

A housing (35) for an electronic device, such as an external component of a cochlear implant system that is powered by one or more batteries (36). The housing comprises a main body portion and a moveable portion (30) operatively associated with the main body portion to enable installation and removal of the batteries (36). The housing (35) includes at least one aperture (31) having a hydrophobic mesh member (33) configured to be positioned at least partially adjacent one or more of the batteries (36) when the batteries are installed in the housing (35).

15 Claims, 8 Drawing Sheets

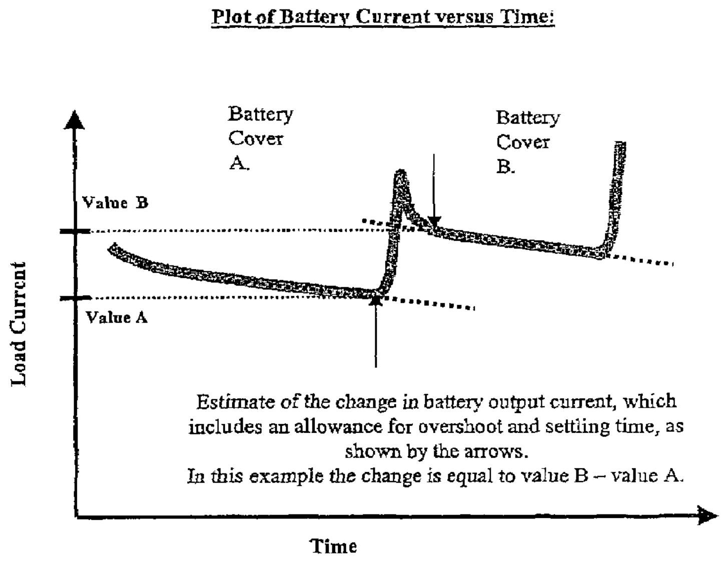

Estimating Changes in Battery Output

FIG. 7

The following percentage increases were observed when the battery covers A (no openings)& B (with hydrophobic mesh) were interchanged (the calculations are done using the values from the graphs):

| Make of battery | Increase in Zn-Air battery current when cover A (no openings) was replaced by cover B (with hydrophobic mesh) | % |
|---|---|---|
| Activair | 5.76mA | 28.09 |
| Toshiba | 6.21mA | 30.91 |
| Rayovac | 4.98mA | 26.15 |
| Varta | 7.63mA | 32.25 |
| Starkey | 2.28mA | 20.65 |

FIG. 8

BATTERY COVER ASSEMBLY

CROSS-REFERENCE TO RELATED APPLICATIONS

This application claims priority from Australian Provisional Patent Application No. 2003905730 filed on Oct. 20, 2003, the contents of which is incorporated herein by reference.

BACKGROUND

1. Field of the Invention

The present invention relates to covers and housings for electronic devices that use miniature batteries.

2. Related Art

Hearing aids and cochlear implants are useful in restoring the sensation of hearing to hearing impaired individuals.

A cochlear implant is used where the hair cells of the cochlea have been damaged to the extent that they are no longer able to convert the mechanical vibration of the cochlea fluid into an electrical signal.

The cochlear implant bypasses the hair cells of the cochlea and delivers electrical stimulation, representative of speech and environmental sounds, to the nerves in the cochlea. The neural impulses generated by this electrical stimulation are then communicated to the brain where they are interpreted as sound.

An example of a cochlear implant system is described in U.S. Pat. No. 4,532,930 ("Crosby"), the contents of which are incorporated herein by reference.

More recently, the physical dimensions of various external components have been able to be reduced. A relatively small unit capable of being worn behind the ear ("BTE") can now house the microphone, batteries and sound processor circuitry.

However, the BTE configuration has increased the likelihood of the components coming into contact with moisture from ambient humidity, precipitation, perspiration, or shower or bath water, causing degradation and corrosion. Similarly, the components can become exposed to contaminants such as dust, hair care products and skin care products.

The above factors can increase the likelihood of intermittent power cut-outs.

It is desired to provide an alternative arrangement that ameliorates the foregoing drawbacks.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In accordance with one aspect of the present invention, there is provided a housing for an electronic device powered by one or more batteries, said housing comprising:

a main body portion; and a moveable portion operatively associated with said main body portion to enable installation and removal of the batteries;

wherein said housing includes at least one aperture having a hydrophobic mesh member configured to be positioned at least partially adjacent one or more of the batteries when the batteries are installed in said housing.

In one embodiment, the at least one aperture can be provided in the movable portion. In this or another embodiment, the hydrophobic mesh member can be a hydrophobic, airflow membrane, such as a membrane formed from ePTFE.

In a further embodiment, the at least one aperture can include two circular portions.

in yet another embodiment, the at least one aperture can further include a screen member that overlays the hydrophobic mesh member. The screen member can be formed from a non-corrosive metal.

In a still further embodiment, the housing can include two apertures.

In a further embodiment, the electronic device can be an external component of a cochlear implant system.

BRIEF DESCRIPTION OF THE DRAWINGS

A preferred form of the present invention will now be described by way of example with reference to the accompanying drawings, wherein:

FIG. 7 is a comparative graph of test results; and

FIGS. 8 and 9 are each a graphs of test results.

DETAILED DESCRIPTION

Before describing the features of the present invention in detail, it is convenient to describe the construction and overall operation of one example of a BTE cochlear implant system.

Figure 1:
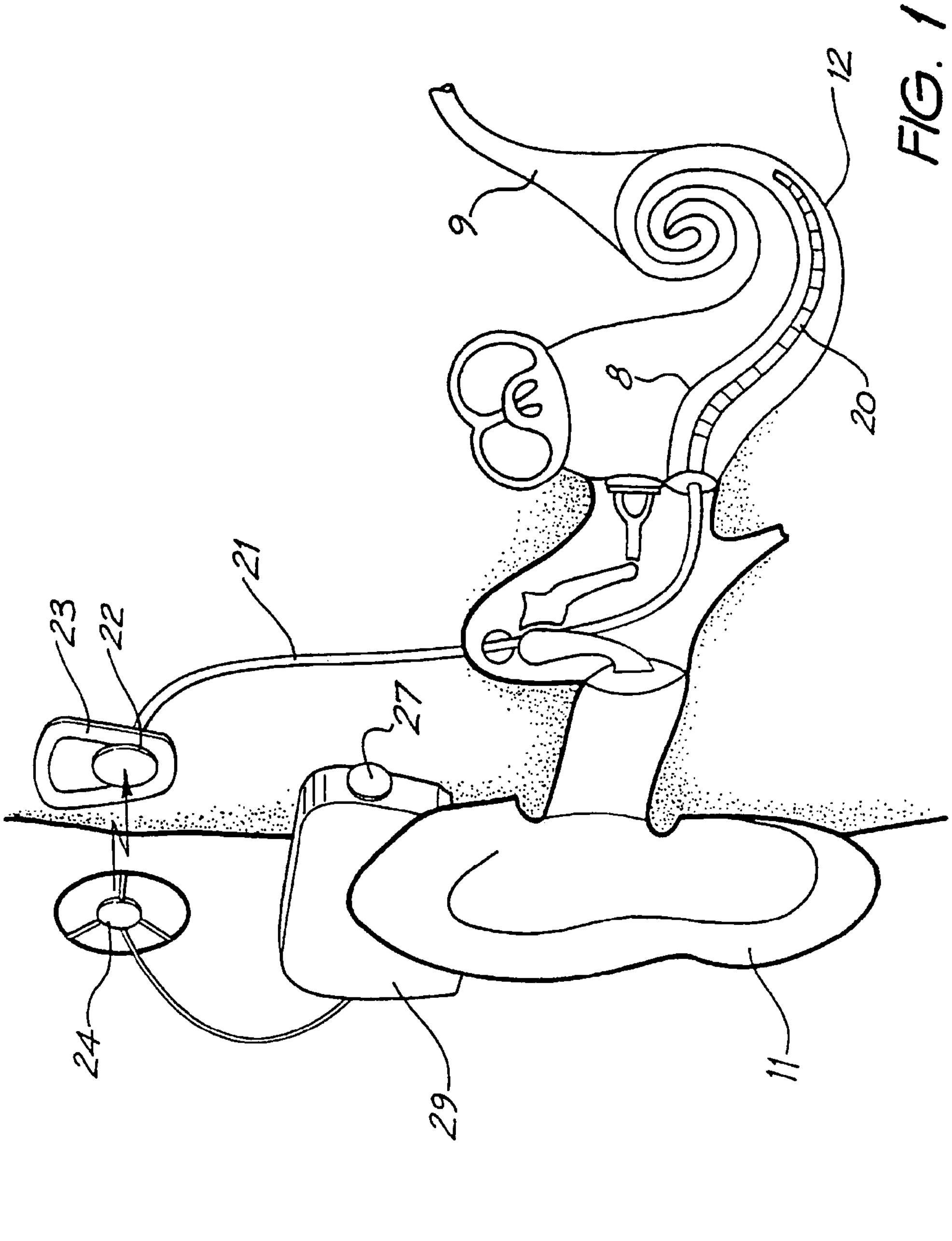
FIG. 1 is an illustrative overview of a BTE cochlear implant system.

Referring to FIG. 1, the fundamental functional components of the cochlear implant system include an external BTE sound processor device 29 connected to an external headset/transmitter antenna coil 24, and an implanted receiver-stimulator 22 connected to an electrode array 20 implanted in the cochlea 12. The external BTE sound processor device 29 includes an on-board microphone 27 and is generally configured to fit behind the outer ear 11, as shown.

In operation, the sound processor device 29 receives sound and calculates a digital data stream, based on a selected coding strategy. The digital data stream thus represents stimulation parameters for application to the electrode array.

The digital data stream is then modulated on to a high frequency (RF) carrier signal, and transmitted together with a power signal, to the implanted receiver-stimulator unit 22 over a transcutaneous radio frequency (RF) link.

The electrical signals received by the receiver antenna coil 23 are provided to the receiver-stimulator unit 22 are applied to the electrode array 20. The electrode array 20 applies electrical stimulation to the basilar membrane 8 and hence the auditory nerve 9 to create a sensation of hearing in the recipient. The electrical stimulation signals are normally bi-phasic and charge balanced to ensure there is no net DC current flow.

It is noted that the receiver coil 23 can also transmit signals back to the transmitter/headset coil 24 for telemetry purposes.

Figure 2:
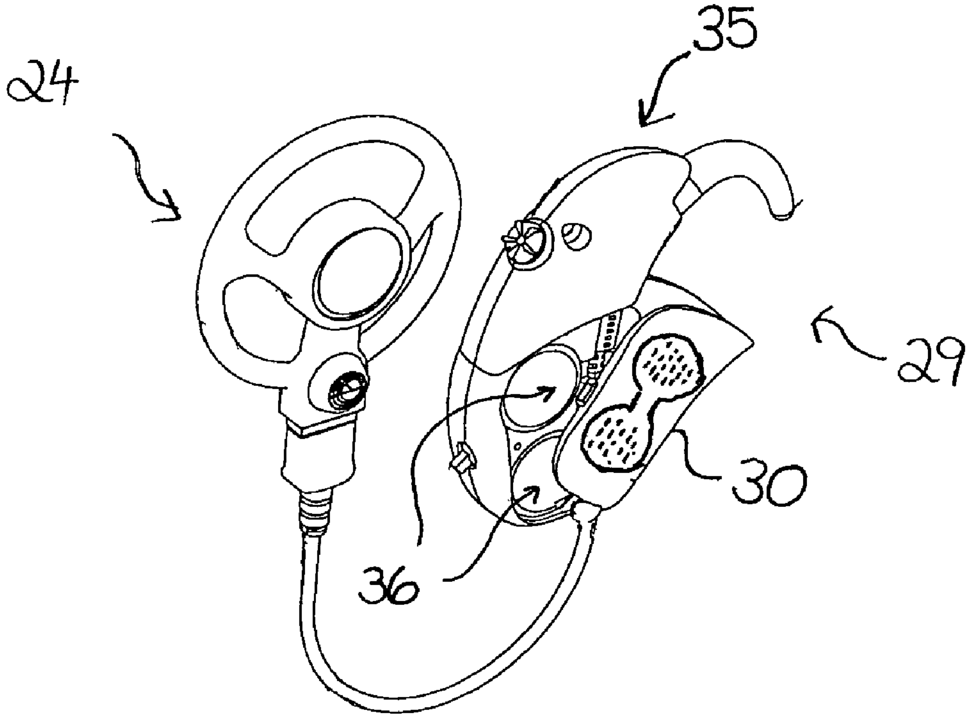
FIG. 2 is a perspective view of a BTE speech processor and headset coil having a battery cover according to one embodiment of the present invention.

Referring now to FIG. 2, a BTE sound processor device 29 according to this disclosure includes a housing 35 for one or more batteries 36, electronic circuitry and the microphone. The housing 35 includes a hinged battery cover 30 that can be selectively opened and closed to enable the batteries 36 to be installed and later replaced. Typically, the batteries 36 will comprise one or more miniature zinc-air button cell batteries connected in series.

Figure 3:
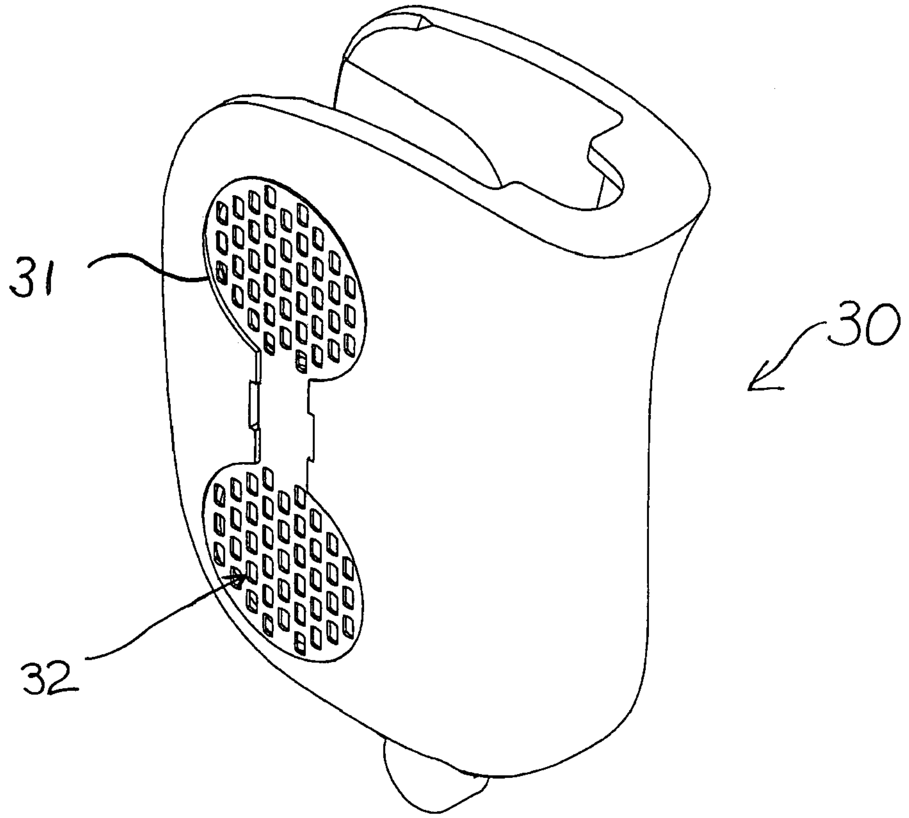
FIG. 3 is a perspective view of the modified battery cover in FIG. 2.

Referring now to FIG. 3, the hinged battery cover 30 includes a shaped opening 31 in one of the two lateral walls. The shaped opening is configured to be generally positioned adjacent and/or over the batteries 36 when the battery cover 30 is closed. In an alternative arrangement, the shaped opening 31 can be provided in both lateral walls of the hinged battery cover 30, while still being generally positioned adjacent and/or over the batteries 36.

In this particular example, the shaped opening 31 includes two circular portions. Each of the circular portions of the shaped opening have a similarly configured ePTFE hydrophobic, airflow membrane 33. An example of a material by which the membrane 33 can be made is Gore-Tex™.

Figure 4:
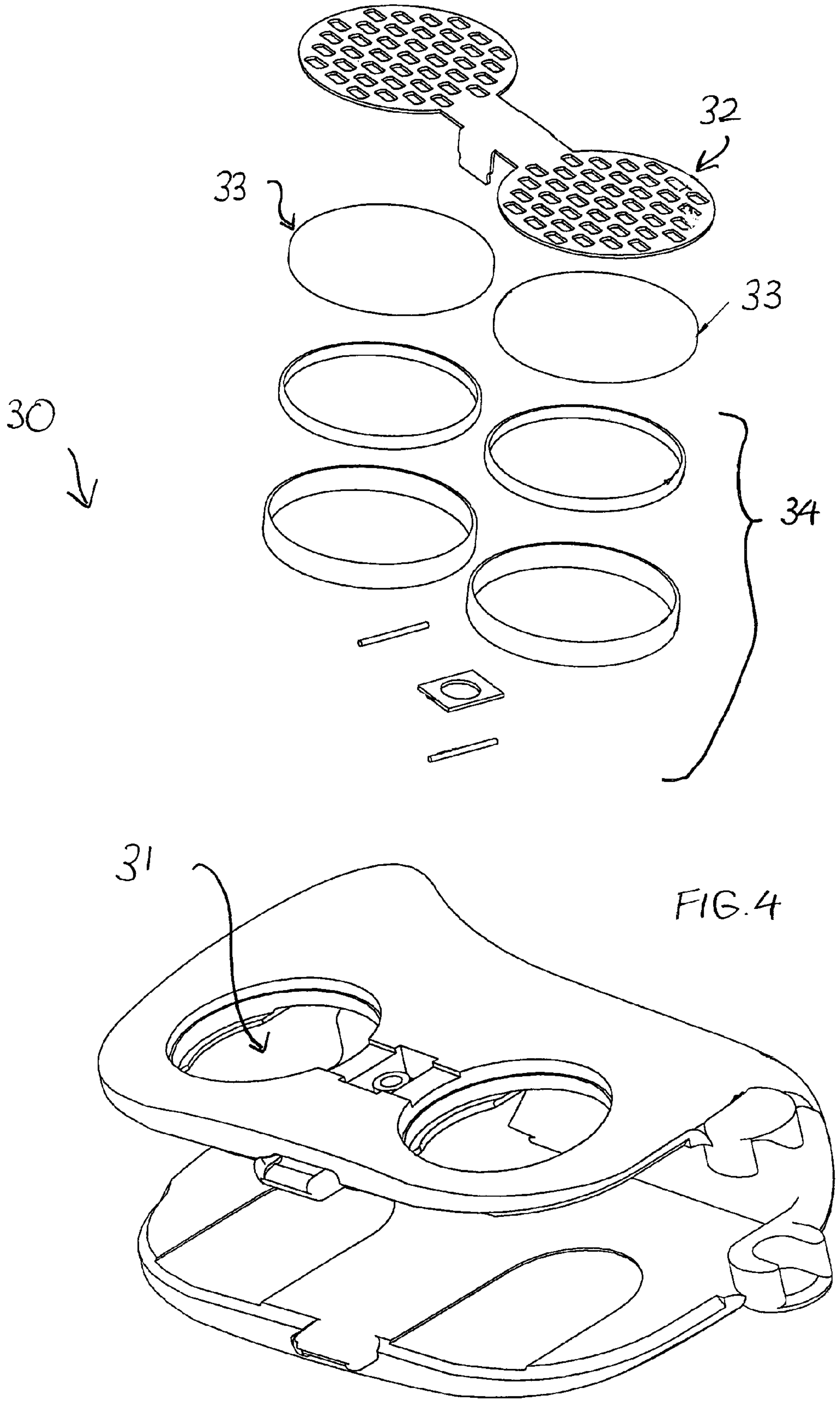
FIG. 4 is an exploded perspective view of the modified battery cover of FIG. 3.

The shaped opening 31 further includes a metallic mesh 32 fitted over each of the membranes 33 as shown, for example, in the exploded perspective view of FIG. 4. A number of holding rings and fixing elements 34 are used to attach the membranes 33 and mesh 32 to the battery cover 30, in a manner that will be generally understood by the person skilled in the art. Accordingly, other methods of attachment for the membranes 33 and mesh 32 are envisaged.

Preferably, the metallic mesh 32 is made from a non-corrosive, biocompatible material and is removable from the battery cover 30, to allow for replacement and service of the membrane 33, the mesh 32 and/or the holding rings and fixing elements 34.

In this example, each membrane 33 is positioned at about halfway between the underside planar surface of the mesh 32 and the upper, or outer surface of the batteries installed in the battery housing 35.

The present inventors have carried out a number of tests on the modified battery cover 30 and have demonstrated that this can provide an advantageous alternative to the prior art arrangements.

Specifically, the test results show that the modified battery cover 30 can improve the current delivery capacity of the batteries 36, thus making more current available for the increasing demands associated with more sophisticated speech processing strategies. As indicated in Table 1, the current capacity of the batteries 36 with the modified battery cover 30 is at least 20% greater at the beginning of the battery life. It is estimated that the current carrying capacity of the batteries 36 is at least 5% greater at the end of battery life.

TABLE 1

The following percentage increases were observed when the battery covers A (no openings) and B (with hydrophobic mesh) were interchanged.

| Make of Battery | Increase in Zn-Air Battery Current when Cover A (no openings) was replaced by Cover B (with hydrophobic mesh) | % |
|---|---|---|
| Activair | 5.76 mA | 28.09 |
| Toshiba | 6.21 mA | 30.91 |
| Rayovac | 4.98 mA | 26.15 |
| Varta | 7.63 mA | 32.25 |
| Starkey | 2.28 mA | 20.65 |

Further, the modified battery cover 30 can reduce the incidence of intermittent faults, thought to have been due to the battery characteristics. The batteries 36 still provide an acceptable mAh capacity and are far less likely to prematurely reach the "low battery cutoff" voltage.

Moreover, the modified battery cover 30 is advantageous when used in high humidity environments or during sporting activities. Any moisture or fluid that happens to creep into the housing of the speech processor device is quickly evaporated, due to an increased airflow that is provided to the interior of the sound processor device.

Figure 5A:
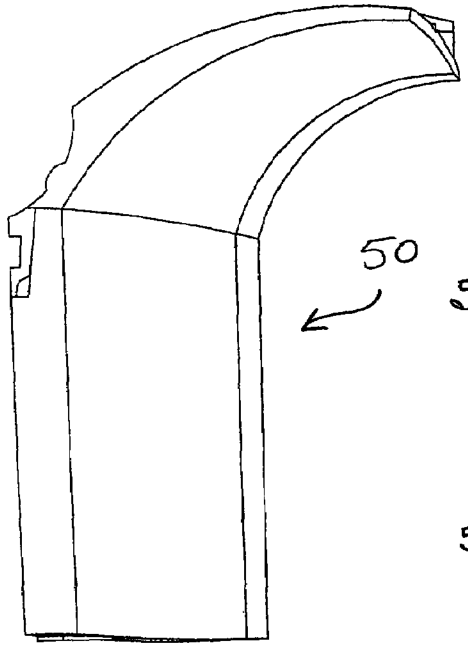
FIGS. 5A to 5C show a number of views of another type of BTE speech processor having an alternative battery cover according to the present invention.
Figure 5B:
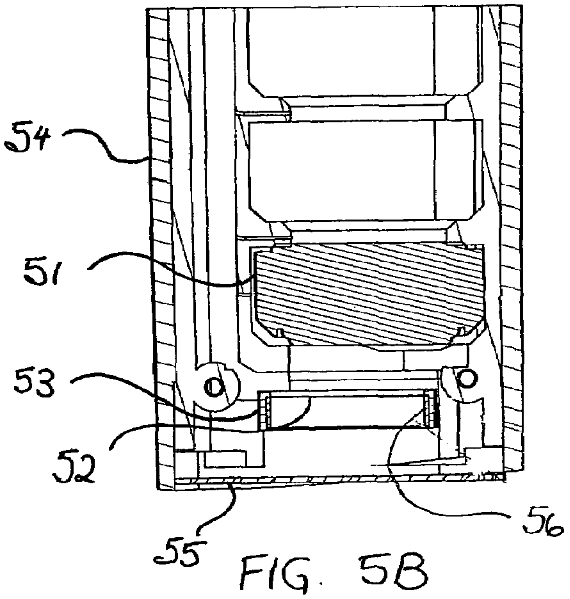
Figure 5C:
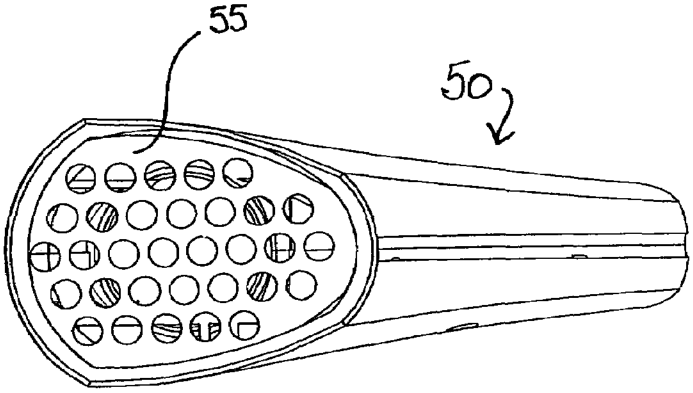

Referring now to FIGS. 5A to 5C, a further example of a modified battery cover is shown. FIG. 5A is a side view of a BTE unit 50, in which the batteries are installed in a battery drawer 51, as shown in the cross sectional view of FIG. 5B. The battery drawer 51 comprises a moveable portion that is adapted to cooperate with a main body portion 54 of the BTE unit 50. The battery drawer 51 operatively allows the batteries associated with powering the BTE unit 50 to be readily installed and replaced.

The battery drawer 51 provides a hydrophobic membrane 52, not unlike that described in relation to the first arrangement, fitted into a membrane mounting assembly 53. The membrane mounting assembly 53 comprises a pair of rings 56 that are adapted to be pressed over the hydrophobic membrane 52, so as to keep the hydrophobic membrane 52 stretched and fixed into position.

The battery drawer 51 is adapted to slide into the main body portion 54 of the BTE unit 50 where it is locked into position. A metallic perforated mesh 55 having a considerable opening area is fitted near the underside of the battery drawer 51, as shown in FIG. 5C.

Test Results

Tests on the present invention were conducted in two phases: Phase 1, where a constant voltage load was applied to the miniature batteries, and Phase 2, where production standard BTE devices were used.

The Phase 1 tests involved connecting the batteries to a 2.2 Volt (V), constant voltage load and measuring the available instantaneous current capacity of the various batteries. This measurement was carried out for a room environment situation, and then repeated for an elevated temperature and humidity.

The Phase 2 set of tests involved connecting the batteries to a working speech processor load, to simulate real-life conditions. The Phase 2 tests also involved testing under periods of no noise, alternating with random noise bursts at regular intervals to cause excess current drain from the batteries.

Figure 6:
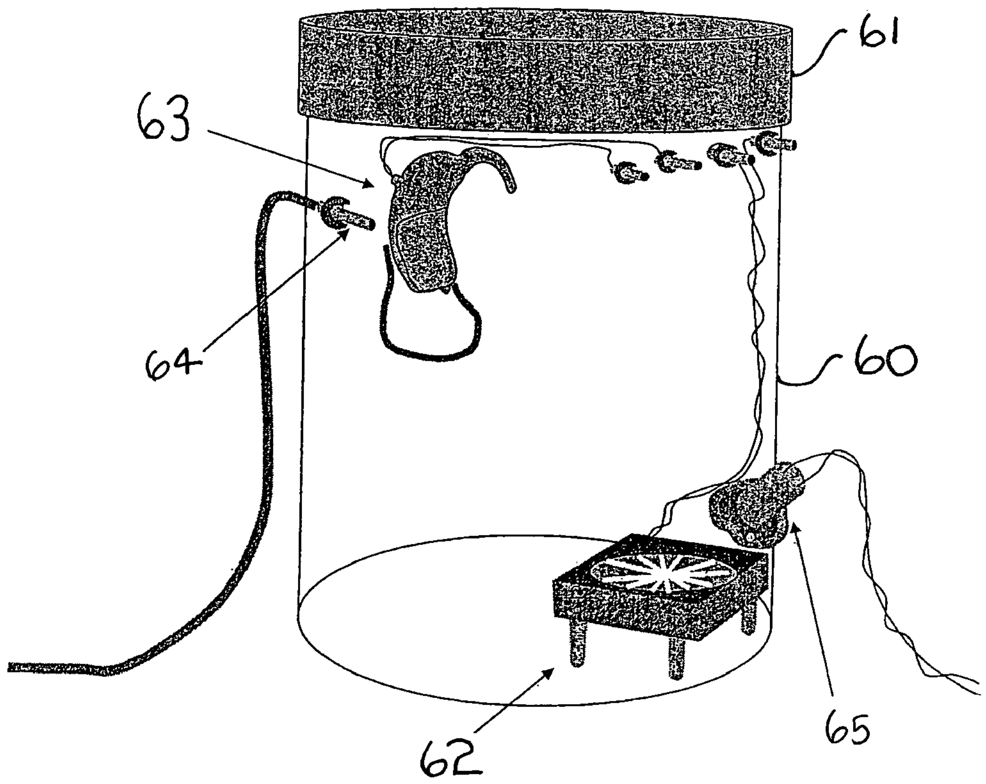
FIG. 6 is a pictorial diagram showing how some of the tests of the battery cover were conducted.

Referring now to FIG. 6, the Phase 1 tests for the room environment situation were carried out in a 4-liter capacity, transparent sided plastic kitchenware container 60 with an airtight lid 61. A constant airflow rate of 0.3 m/s was provided by a brushless DC fan 62, spaced about 15 mm above the base of the container 60. A thermocouple probe 64 was used to measure temperature. The fan speed was set and verified using a stroboscope constructed with a red LED, fixed to the container, and connected to a function generator. An example of a BTE unit undergoing testing is depicted generally as 63 in FIG. 6.

The elevated temperature and humidity conditions were achieved using an oven set at 30° C., and in which a 500 ml beaker holding approximately 250 ml of water was placed inside. After around 20 mins, sufficient humidity was developed in the oven and the tests could be conducted.

The test schedule was as follows:

| Load Circuit | Covers under test | Conditions |
|---|---|---|
| 2.2 V constant voltage load with different batteries | (i) prior art cover<br>(ii) no cover<br>(iii) modified cover | At room condition:<br>20° C. (±5° C.) and RH 55% (±10%) |
| 2.2 V constant voltage load with different batteries | (i) prior art cover<br>(ii) modified cover | Elevated temperature and humidity:<br>30°(±5° C.)/85%(±4% C) RH, at 40°/95% RH |
| 3 × BTE units | (i) prior art cover<br>(ii) modified cover | At room condition with sound bursts |

RH = Relative Humidity

In all cases, the tabs of the batteries were removed and allowed to activate in air for around 5 minutes before being tested.

Phase 1, Part A: Tests at Room Environment

This test was conducted for different makes of batteries. The two series-connected battery cells were placed in a dummy battery holder without any cover and placed on the inside wall of the test container 60, using a non permanent, adhesive putty. The dummy battery holder without a cover provides a baseline because this represents a maximum current output that may be obtained from a battery during test.

A constant voltage load circuit was then applied, so as to maintain a load of between 2.200 and 2.199 volts DC. The discharge current from the batteries was then logged for 10 minutes.

A prior art battery cover was then placed over the dummy battery holder and the 10 minute discharge test was repeated. Similarly, the modified battery cover was fitted to the dummy battery holder and the 10 minute discharge test again repeated.

Finally, the batteries were allowed to discharge without any cover, until the discharge current fell to 14 mA, thus providing an 'end of life' series of readings.

Phase 1, Part B: Tests in Elevated Temperature and Humidity Conditions

As earlier discussed, this test was set up by placing a 500 ml beaker filled with approx. 250 ml water in an oven set to 30° C. for about 20 minutes. A humidity meter was used to verify the required humidity parameters as set out in the test schedule.

The batteries were placed in the dummy battery holder and a prior art cover fitted. The 2.2V constant voltage load was connected and the holder suspended just above the beaker while current readings were recorded until the end of the battery life.

This test was carried out for at least two different makes of batteries with both the prior art cover and the modified cover.

Phase 2: Tests with Working Speech Processors

This test was conducted only with Toshiba 675 SP batteries, as the differences between the battery cover designs with different makes of batteries was already tested in Phase 1.

The test was performed for each of three BTE speech processors having a MAP selected to elicit maximum speech processor power consumption (e.g. high pulse width, high T & C levels, high number of maxima etc). The sensitivity control was kept at maximum during all tests.

Firstly, the batteries were placed in a dummy battery holder with a prior art battery cover. The holder was placed on the inside wall of the container using adhesive putty and the airflow set as per phase 1. The output terminals of the dummy battery holder were connected to the battery terminals of the BTE device under test, with an ammeter in series and a voltmeter in parallel.

An RF coil connected to the BTE device was then coupled to a receiver circuit in an 'implant in a box' system. An 'implant in a box system' is one constructed for the specific purpose of simulating the working of a BTE device under test.

To stimulate the sudden bursts of sound in real life, a signal generator was used to supply a sine wave burst of 4 KHz to a pair of speakers placed approximately 25 cm from the speech processor. The amplitude of the sine wave bursts was set so that at the sound burst, the current supplied by the batteries was 18 mA (±2 mA).

The current consumption and battery voltage during the sound burst tests was logged at 2 second intervals. In particular, the readings were monitored for any sudden change in the current/voltage, as more intermittency may be expected at the end of the battery life. Intermittency was identified by a sudden fall of current, to a value less than 1 mA.

Next the prior art battery cover was replaced with the modified battery cover and the test repeated.

The covers were swapped at least 3 times at 30 minutes time intervals and the changes in the supply voltage/current of the battery were monitored. These steps were repeated at the end of battery life period.

Referring now to FIG. 7, the test results were documented and are shown here in the form of a plot of battery current v. time, for the prior art battery cover ("A") and the modified battery cover ("B"). Importantly, these test results show that for a constant load, the batteries in the modified cover (B) provided an increase in available battery current, in comparison with batteries in the prior art cover(A).

Figure 9:
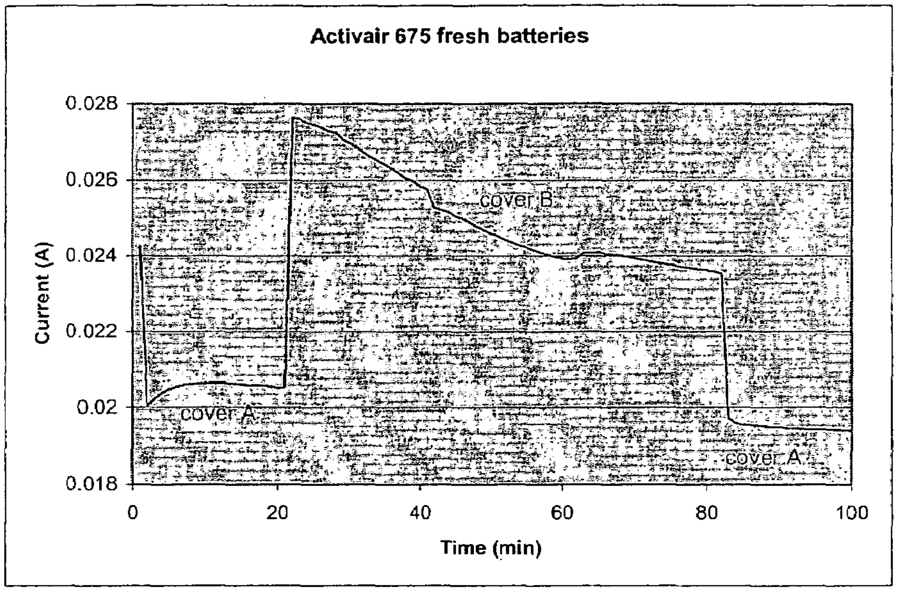
Figure 10:
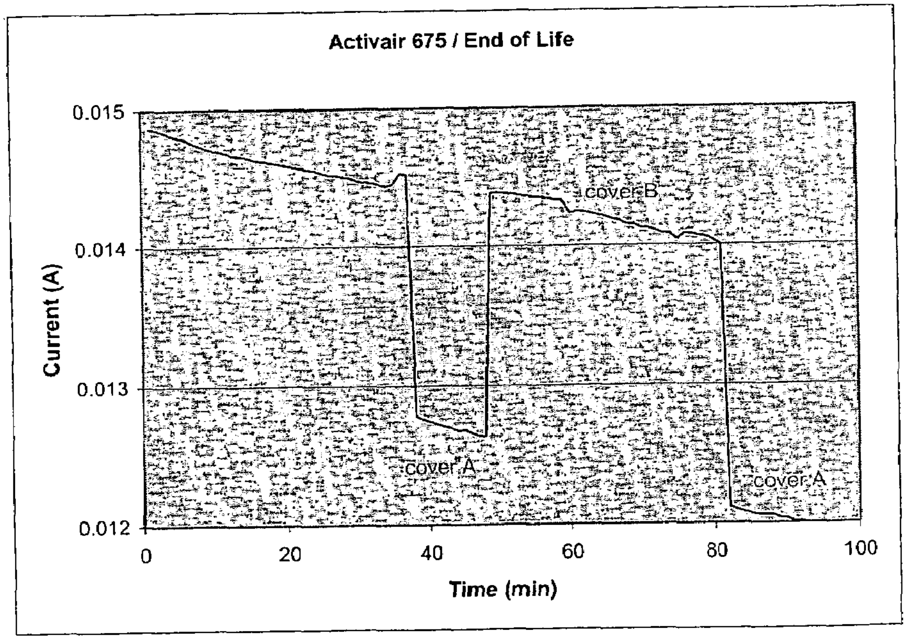

FIGS. 8 and 9 are each a discharge graph, showing the current delivery of batteries under a constant voltage load of 2.2 volts, for each of the (i) no cover, (ii) prior art cover (A), and (iii) modified cover (B) tests. FIG. 8 shows that there is a minimal difference between the performance of the zinc-air batteries in free air, compared with the same batteries using the modified cover. Moreover, FIG. 9 shows a marked improvement in the performance of the zinc-air batteries when tested with the modified cover (B), in comparison with the prior art cover (A).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A housing for an electronic device powered by one or more batteries disposed within the housing, said housing comprising:

a main body portion, configured to receive the one or more batteries;

at least one aperture within said housing;

a moveable portion, configured to be coupled with said main body portion, and further configured to be removable to enable installation and removal of the one or more batteries;

a hydrophobic airflow membrane disposed within said aperture and at least partially adjacent to at least one of the one or more batteries when the one or more batteries are disposed within said housing; and a mesh, comprising a plurality of adjacent apertures, configured to overlay the hydrophobic airflow membrane.

2. The housing according to claim 1, wherein said aperture is disposed in the movable portion.

3. The housing according to claim 1, wherein the membrane is ePTFE.

4. The housing according to claim 1, wherein said aperture includes two circular portions.

5. The housing according to claim 1, wherein the mesh is a non-corrosive metallic mesh.

6. The housing according to claim 1, wherein said housing comprises two apertures.

7. The housing according to claim 1, wherein the electronic device is an external component of a cochlear implant system.

8. A method of sealing a housing of an electronic device powered by one or more batteries, the housing having at least one aperture and a main body portion configured to receive the one or more batteries, a moveable portion configured to be coupled to the main body portion, a hydrophobic airflow membrane configured to provide a moisture seal and further configured to allow airflow through the hydrophobic airflow membrane, and a mesh, comprising a plurality of adjacent apertures, comprising:

providing the main body portion;

inserting the hydrophobic airflow membrane within the at least one aperture of the housing thereby providing airflow and a moisture-seal for the housing; and overlaying the mesh on the hydrophobic airflow membrane.

9. The method according to claim 8, wherein said at least one aperture is disposed in the movable portion.

10. The method according to claim 8, wherein the hydrophobic airflow membrane is a hydrophobic airflow membrane.

11. The method according to claim 10, wherein the membrane is ePTFE.

12. The method according to claim 8, wherein said at least one aperture comprises two circular portions.

13. The method according to claim 8, wherein the mesh is a non-corrosive metallic mesh.

14. The method according to claim 8, wherein said housing comprises two apertures.

15. The method according to claim 8, wherein the electronic device is an external component of a cochlear implant system.

* * * * *